(12) United States Patent
Madderson et al.

(10) Patent No.: US 10,598,602 B2
(45) Date of Patent: Mar. 24, 2020

(54) METHOD AND SYSTEM FOR DETECTING A DIAMOND SIGNATURE

(71) Applicant: Tomra Sorting GmbH, Mülheim-Kärlich (DE)

(72) Inventors: Geoffrey Harold Madderson, Johannesburg (ZA); Markus Dehler, Wedel (DE)

(73) Assignee: TOMRA SORTING GMBH, Müllheim-Kärlich (DE)

( * ) Notice: Subject to any disclaimer, the term of this patent is extended or adjusted under 35 U.S.C. 154(b) by 0 days.

(21) Appl. No.: 16/344,179

(22) PCT Filed: Oct. 24, 2017

(86) PCT No.: PCT/EP2017/077143
§ 371 (c)(1),
(2) Date: Apr. 23, 2019

(87) PCT Pub. No.: WO2018/077866
PCT Pub. Date: May 3, 2018

(65) Prior Publication Data
US 2019/0317023 A1    Oct. 17, 2019

(30) Foreign Application Priority Data

Oct. 24, 2016   (EP) .................................... 16195384

(51) Int. Cl.
*G01N 21/00* (2006.01)
*G01N 21/87* (2006.01)
(Continued)

(52) U.S. Cl.
CPC ........... *G01N 21/87* (2013.01); *B07C 5/3425* (2013.01); *G01N 21/359* (2013.01); *G01N 21/85* (2013.01);
(Continued)

(58) Field of Classification Search
CPC .. G01N 21/87; G01N 33/381; G01N 21/8806; G01N 21/64; G01N 21/65
(Continued)

(56) References Cited

U.S. PATENT DOCUMENTS 5,206,699 A    4/1993  Stewart et al.
7,768,643 B1   8/2010  Janssens et al.
(Continued)

FOREIGN PATENT DOCUMENTS

DE    202004009165 U1    10/2004
EP         2392414 A1    12/2011
(Continued)

OTHER PUBLICATIONS

International Search Report (PCT/ISA/210) dated Feb. 13, 2018, by the European Patent Office as the International Searching Authority for International Application No. PCT/EP2017/077143.
(Continued)

*Primary Examiner* — Md M Rahman
(74) *Attorney, Agent, or Firm* — Buchanan Ingersoll & Rooney P.C.

(57) ABSTRACT

A method for identifying the presence of partly liberated diamonds in a material stream. The method can include illuminating a material with a multi-wavelength beam including at least one monochromatic SWIR laser beam, and at least one IR scatter-/anti-scatter laser beam, capturing a portion of the at least one monochromatic SWIR laser beam after the monochromatic SWIR laser beam has been reflected and/or scattered by the material, producing a SWIR signal based on the captured portion of the at least one monochromatic SWIR laser beam, and capturing a first portion of the at least one IR scatter-/anti-scatter laser beam after the at least one IR scatter-/anti-scatter laser beam has been scattered and optionally reflected by the material.

14 Claims, 8 Drawing Sheets

(51) Int. Cl.
  *B07C 5/342* (2006.01)
  *G01N 21/359* (2014.01)
  *G01N 21/85* (2006.01)
  *G01N 33/38* (2006.01)

(52) U.S. Cl.
  CPC .... *G01N 33/381* (2013.01); *B07C 2501/0018* (2013.01)

(58) Field of Classification Search
  USPC .......................................................... 356/30
  See application file for complete search history.

(56) References Cited

U.S. PATENT DOCUMENTS

| 2010/0290040 | A1 | 11/2010 | Berghmans |
| 2013/0135461 | A1 | 5/2013 | Schmidt et al. |
| 2016/0252461 | A1 | 9/2016 | Harbeck et al. |

FOREIGN PATENT DOCUMENTS

| WO | 2013135816 | A1 | 9/2013 |
| WO | 2015063300 | A1 | 5/2015 |

OTHER PUBLICATIONS

Written Opinion (PCT/ISA/237) dated Feb. 13, 2018, by the European Patent Office as the International Searching Authority for International Application No. PCT/EP2017/077143.

METHOD AND SYSTEM FOR DETECTING A DIAMOND SIGNATURE

FIELD OF THE INVENTION

The present invention relates to diamond detection, for example in the detection of non-liberated diamonds in a flow of rock particles, such as Kimberlite.

BACKGROUND

While working in the diamond recovery field and supplying of diamond recovery technologies the problem of non-liberated and partly-liberated diamonds has been observed. Non-liberated diamonds are those still attached to rock product/particles/gravel such as Kimberlite and other minerals. These non-liberated diamonds can then in turn be misplaced in the beneficiation process, which can result in them being misplaced during dense media separation, DMS, due to their density being below the cut point of the DMS Cyclone and subsequently sent to the tailings.

Non-liberated diamonds can also be damaged/stressed or severely broken while in the circuit due to them not reporting to the recovery section of the plant, but then reporting to the crushing section and then in turn being broken as the size of the material is reduced to pass the CSS which then in turn damages the diamonds. This constitutes a preventable and unnecessary value loss for a mining company that is processing the deposit, and for the government that receives royalties and taxes on the sale of the diamonds.

Prior art diamond detection involves excitation by a laser beam and measurement of the laser light scattered by the crystalline structure of diamonds. By using the property of diamonds to scatter light within their crystalline structure and the effect of "Glowing" or "Lighting Up" the area around the direct reflection, it is possible to use this as a signature to discriminate the diamonds from rock product or particles/gravel such as Kim berlite and other minerals even if the diamond is only partly liberated and still attached to the gravel. The disadvantage of this basic principle is that other transmissive minerals like Quartz, some calcite etc. scatter as well and may be misplaced in a sorting process resulting in higher yield.

Other prior art documents describe other methods for detecting a target material in a material stream, such as the method described in EP2392414, which method involves illuminating a material stream with light having a pre-determined spectral bandwidth, said pre-determined bandwidth being in the proximity of the Full Width at Half Maximum value of the spectral peak of the target material that is to be detected; whereafter reflections and scattered light from the illumination means are captured and analyzed.

It is therefore an object of the invention to come up with a high-speed process for the improved recovery of partly liberated diamonds that would otherwise be damaged or lost. It is a further aim to improve diamond detection. It is a further aim to improve diamond value management by providing suitable diamond recovery technologies to suit a wider variety of ore types.

The object of the present invention is to overcome or alleviate at least one of the abovementioned problems. This is achieved by a method as defined in the independent claim. Advantageous embodiments of the present invention are derived from the subclaims and the following description.

It was surprisingly found that using at least one monochromatic SWIR laser beam can be advantageously used for recovery of partly liberated diamonds in a precise and reliable manner. This finding is surprising as choosing the bandwidth for the illuminating beam is usually done by taking the Full Width at Half Maximum value of the spectral peak of the target material that is to be detected. The rationale behind this is that the skilled person knows that a certain bandwidth is necessary in order to achieve reliability in the detection of diamond in a material stream. The skilled person knows that using a smaller bandwidth means that the method risks missing diamonds that, due to various reasons, may have a slightly different spectral peak than those which the diamond detector is arranged to detect.

SUMMARY OF THE INVENTION

According to the present invention there is provided a method for identifying the presence of partly liberated diamonds in a material stream, said method comprising the steps of:

illuminating a material with a multi-wavelength beam comprising at least one monochromatic SWIR laser beam, and at least one IR scatter-/anti-scatter laser beam, capturing a portion of said at least one monochromatic SWIR laser beam after said monochromatic SWIR laser beam has been reflected and/or scattered by the material, producing a SWIR signal based on the captured portion of said at least one monochromatic SWIR laser beam, capturing a first portion of said at least one IR scatter-/anti-scatter laser beam after said at least one IR scatter-/anti-scatter laser beam has been scattered and optionally reflected by the material, separating and thereafter capturing a reflected portion of said at least one IR scatter-/anti-scatter laser beam after said at least one IR scatter-/anti-scatter laser beam has been reflected by the material from a portion of said at least one IR scatter-/anti-scatter laser beam after said at least one IR scatter-/anti-scatter laser beam has been scattered by the material, producing an IR scatter signal based on said captured first portion of said at least one IR scatter-/anti-scatter laser beam, producing an IR reflection signal based on said captured reflected portion of said at least one IR scatter-/anti-scatter laser beam, classifying the material as comprising diamond based on the presence of a diamond signature in the combination of the SWIR signal, the IR reflection signal and the IR scatter signal.

In one example embodiment, the IR scatter signal is a IR combined reflection and scatter signal, based on said captured first portion of said at least one IR scatter-/anti-scatter laser beam and a captured second portion of said at least one IR scatter-/anti-scatter laser beam after said second portion of said at least one IR scatter-/anti-scatter laser beam has been reflected by the material. The skilled person readily understands that either one of the IR scatter signal and the IR combined reflection and scatter signal may be used in the classification of material.

Capturing SWIR reflections from the material may comprise reflecting SWIR wavelengths to a SWIR detector.

Separating the scattered light from the reflected light and capturing only the reflections of the incident beam may comprise detecting in a field of view corresponding in size to the size of the incident beam.

The method may comprise focusing the reflected light before capture. The method may comprise splitting a beam of the light after it has been reflected or scattered by the material to capture both the IR reflection signal and the IR scatter signal. The method may comprise converting each of the SWIR signal, the IR scatter signal, and the IR reflection signal into digital signals.

According to one exemplary embodiment, the method further comprises the step of separating a first portion of said at least one IR scatter-/anti-scatter laser beam after said at least one IR scatter-/anti-scatter laser beam has been scattered by the material from a portion of said at least one IR scatter-/anti-scatter laser beam after said at least one IR scatter-/anti-scatter laser beam has been reflected by the material, and thereafter capturing said first portion of said at least one IR scatter-/anti-scatter laser beam.

Thus, a reflected portion of said at least one IR scatter-/anti-scatter laser beam may be separated from a scattered portion of said at least one IR scatter-/anti-scatter laser beam, and vice versa. A reflected portion of said at least one IR scatter-/anti-scatter laser beam may then be captured and used to produce an IR reflection signal. A scattered portion of said at least one IR scatter-/anti-scatter laser beam may then be captured and used to produce an IR scatter signal.

According to one exemplary embodiment, the step of separating a reflected portion of said IR scatter-/anti-scatter laser beam is done by optically filtering scattered light from reflected light. This step may alternatively be done by capturing both the reflected and scattered portion of said IR scatter-/anti-scatter laser beam and subtracting the captured reflected portion of said IR scatter-/anti-scatter laser beam therefrom. Thus, a scatter signal may be achieved either by means of e.g. a mechanical mask filtering reflected light from scattered light, or by means of subtracting reflected light from light that has been both reflected and scattered.

According to one exemplary embodiment, the step of separating a first portion of said IR scatter-/anti-scatter laser beam is done by optically filtering reflected light from scattered light.

According to one exemplary embodiment, wherein said at least one IR scatter-/anti-scatter laser beam is at least one monochromatic IR scatter-/anti-scatter laser beam.

According to one exemplary embodiment, the method further comprises the step of filtering out light having the same polarization as the incident beam, so that only cross-polarized light is captured.

According to one exemplary embodiment, the method further comprises the step of splitting said IR scatter-/anti-scatter laser beam.

According to one exemplary embodiment, the method further comprises the step of normalizing the SWIR signal and the IR scatter signal by dividing each by the IR reflection signal.

According to one exemplary embodiment, the method further comprises the step of scanning said multi-wavelength beam across said material stream.

According to one exemplary embodiment, the material stream comprises at least one rock particle having a partly liberated diamond.

According to one exemplary embodiment, the method further comprises forming a two-dimensional space using the normalized SWIR signal and the normalized IR scatter signal to represent the material.

According to one exemplary embodiment, the two-dimensional space represents multiple rock particles.

According to one exemplary embodiment, the method further comprises classifying pixels within the two-dimensional space as diamond or other material classes.

According to one exemplary embodiment, the method further comprises ejecting objects comprising material classified as diamond from a transportation direction of said material stream.

The multi-wavelength beam of IR light may comprise multiple beams of IR light combined in one common beam. The multi-wavelength beam of IR light may comprise three beams of IR light combined in one common beam, wherein at least one beam is a beam of SWIR light. The method may comprise scanning the beam across the material.

The material may comprise multiple rock particles. The multiple rock particles may form part of a flow of rock particles.

The method may comprise forming a two-dimensional space using the normalized SWIR signal and the normalized IR scatter signal to represent the material. The method may comprise classifying pixels within the two-dimensional space as diamond or other material classes. The two-dimensional space may represent a single rock particle. The two-dimensional space may represent multiple rock particles.

The method may be used in a sorting process, wherein objects comprising material classified as diamond may be ejected from a flow path of objects to be sorted.

According to one aspect of the invention, there is provided an apparatus comprising means for illuminating a material with a multi-wavelength beam comprising at least one monochromatic SWIR laser beam, and at least one IR scatter-/anti-scatter laser beam, means for capturing a portion of said at least one monochromatic SWIR laser beam after said monochromatic SWIR laser beam has been reflected and/or scattered by the material, means for producing a SWIR signal based on the captured portion of said at least one monochromatic SWIR laser beam;

means for capturing a first portion of said at least one IR scatter-/anti-scatter laser beam after said at least one IR scatter-/anti-scatter laser beam has been scattered and optionally reflected by the material, means for separating and thereafter capturing a reflected portion of said at least one IR scatter-/anti-scatter laser beam after said at least one IR scatter-/anti-scatter laser beam has been reflected by the material from a portion of said at least one IR scatter-/anti-scatter laser beam after said at least one IR scatter-/anti-scatter laser beam has been scattered by the material, means for producing an IR scatter signal based on said captured first portion of said at least one IR scatter-/anti-scatter laser beam;

means for producing an IR reflection signal based on said captured reflected portion of said at least one IR scatter-/anti-scatter laser beam means for classifying the material as comprising diamond based on the presence of a diamond signature in the combination of the SWIR signal, the IR reflection signal and the IR scatter signal.

The means for capturing SWIR reflections from the material may comprise means for reflecting SWIR wavelengths to a SWIR detector. The means for reflecting SWIR wavelengths to a SWIR detector may comprise a dichroic mirror. The means for filtering out the scattered light and capturing only the reflections of the incident beam may comprise means for detecting in a field of view corresponding in size to the size of the incident beam. The means for detecting in a field of view corresponding in size to the size of the incident beam may comprise a detector with an aperture with a diameter corresponding substantially to the cross-sectional diameter of the incident beam. The aperture may be defined in a plate or diaphragm. The means for capturing the remaining reflections or scattered light from the material and means for producing an IR combined reflection and scatter signal or an IR scatter signal may comprise a detector with a field of view larger than that of the detector for capturing only the reflections of the incident beam, wherein there is an optical filter or mechanical mask arranged to filter out light directly reflected by the material. Said optical filter or mechanical mask may be a round disc. Said round disc may be coaxially aligned with the reflected portion of the incident beam.

Additionally or alternatively, said means for separating a reflected portion of said at least one IR scatter-/anti-scatter laser beam after said at least one IR scatter-/anti-scatter laser beam has been reflected by the material from a portion of said at least one IR scatter-/anti-scatter laser beam after said at least one IR scatter-/anti-scatter laser beam has been scattered by the material is for example a pin hole, diaphragm, or other known means. Said pin hole or diaphragm may be arranged to allow the center of the reflected beam to pass therethrough and block out a scattered portion of the light.

The apparatus may comprise means for filtering out light having the same polarization as the incident beam, so that only cross-polarized light is captured. The means for filtering may comprise a polarizing beam splitter. The apparatus may comprise means for focusing the reflected light before capture. The means for focusing may comprise at least one focusing lens. The apparatus may comprise means for splitting a beam of the light reflected and scattered by the material to capture both the IR reflection signal and the IR scatter signal. The means for splitting may be a non-polarizing beam splitter.

The apparatus may comprise means for converting each of the SWIR signal, the IR scatter signal, and the IR reflection signal into digital signals. The means for converting may be a digital to analog converter. The apparatus may comprise means for normalizing the SWIR signal and the IR scatter signal by dividing each by the IR reflection signal.

The multi-wavelength beam of IR light may comprise multiple beams of IR light combined in one common beam. The apparatus may comprise a first IR laser and a second SWIR laser. The apparatus may comprise means for combining multiple beams of IR light into one common beam. The means may comprise one or more dichroic mirrors. The multi-wavelength beam of IR light may comprise three beams of IR light combined in one common beam, wherein at least one beam is a beam of SWIR light.

The apparatus may comprise means for scanning the beam across the material. The means for scanning the beam across the material may comprise a rotating polygon mirror.

The material may comprise multiple rock particles. The multiple rock particles may form part of a flow of rock particles.

The apparatus may comprise means for forming a two-dimensional space using the normalized SWIR signal and the normalized IR scatter signal to represent the material.

The apparatus may comprise classifying pixels within the two-dimensional space as diamond or other material classes. The two-dimensional space may represent a single rock particle. The two-dimensional space may represent multiple rock particles.

According to one embodiment of the invention, said method is performed by an apparatus comprising:

means for illuminating a material with a multi-wavelength beam comprising at least one monochromatic SWIR laser beam, and at least one IR scatter-/anti-scatter laser beam, means for capturing a portion of said at least one monochromatic SWIR laser beam after said monochromatic SWIR laser beam has been reflected and/or scattered by the material, means for producing a SWIR signal based on the captured portion of said at least one monochromatic SWIR laser beam;

means for capturing a first portion of said at least one IR scatter-/anti-scatter laser beam after said at least one IR scatter-/anti-scatter laser beam has been scattered and optionally reflected by the material, means for separating and thereafter capturing a reflected portion of said at least one IR scatter-/anti-scatter laser beam after said at least one IR scatter-/anti-scatter laser beam has been reflected by the material from a portion of said at least one IR scatter-/anti-scatter laser beam after said at least one IR scatter-/anti-scatter laser beam has been scattered by the material, means for producing an IR scatter signal based on said captured first portion of said at least one IR scatter-/anti-scatter laser beam;

means for producing an IR reflection signal based on said captured reflected portion of said at least one IR scatter-/anti-scatter laser beam means for classifying the material as comprising diamond based on the presence of a diamond signature in the combination of the SWIR signal, the IR reflection signal and the IR scatter signal, and said process comprising the step of ejecting material classified as comprising diamond from the material stream that is to be sorted.

According to one exemplary embodiment of the present invention, said apparatus further comprises means for scanning the beam across the material.

According to one exemplary embodiment of the present invention, said means for scanning the beam across the material comprises a rotating polygon mirror.

According to one exemplary embodiment of the present invention, said means for illuminating a material with a multi-wavelength beam is at least one monochromatic SWIR laser, and at least one monochromatic IR laser.

According to one exemplary embodiment of the present invention, said means for capturing a portion of said at least one monochromatic SWIR laser beam after said monochromatic SWIR laser beam has been reflected and/or scattered by the material is a single PIN diode.

According to one exemplary embodiment of the present invention, said means for capturing a first portion of said at least one IR scatter-/anti-scatter laser beam after said at least one IR scatter-/anti-scatter laser beam has been scattered and optionally reflected by the material is a single PIN diode.

According to one exemplary embodiment of the present invention, said means for capturing a reflected portion of said at least one IR scatter-/anti-scatter laser beam after said at least one IR scatter-/anti-scatter laser beam has been reflected by the material is a single PIN diode.

According to one exemplary embodiment of the present invention, said means for separating a reflected portion of said at least one IR scatter-/anti-scatter laser beam from a scattered portion of said at least one IR scatter-/anti-scatter laser beam is an optical filter.

According to the present invention there is further provided a sorting system comprising an apparatus as defined above, further comprising means for ejecting objects comprising material classified as diamond from a flow path of objects to be sorted. The means for ejecting objects may be adapted to eject objects while falling.

According to the present invention there is further provided a computer readable medium containing program instructions which when executed by a processor cause the processor to perform the above method.

The apparatus for identifying a diamond signature may form part of a laser scanner. Multiple laser scanners may be provided in a sorting system.

Where multiple lasers are provided, each may produce a concentrated beam of light. The beams of light may be combined into one common beam. A polarizing beam splitter may be used to remove any irregularity in the polarization of the common beam.

Means for directing the beam onto the product may be provided and may comprise at least one mirror. The at least one mirror may comprise a rotatable mirror with multiple faces. One possible rotatable mirror is a polygon mirror.

At least one laser preferably operates in the range 700 to 1000 nm. For example in the range of 800 to 900 nm, or at 730 nm or at 830 nm. At least one laser operates in the range 1100 to 1700 nm, for example in the range of 1110 to 1600 nm, or in the range of 1450 to 1550 nm, or at 1490 nm. At least one additional laser may be provided, for example operating in the range 1100 to 1700 nm, for example in the range of 1110 to 1600 nm, or in the range of 1400 to 1600 nm, or at 1550 nm.

By combining the IR scatter signal, the IR reflection signals and the SWIR signal, one gets a signature for diamond which is distinctive and unique. This means that the misplacement of gravel diluting the concentrate is minimized, thus resulting in lower yield with higher purity of the diamond concentrate without compromising the high recovery rate.

The method may be used to detect diamond in a flow of rock particles where at least one laser beam may be directed toward the rock particle flow as it moves through a detection zone. The laser beams may form part of a light band which moves transversely across the path of the rock particles wherein at least one detector is arranged to detect reflected and scattered light.

By "scattered light" is meant in this description on the one hand the light which is diffusely reflected at the surface of a product, and on the other hand the light that is emitted by the product as a result of said light band at least partly penetrating it, spreading into it, and thereby making the corresponding part of the product light up.

The rock particles may be presented as a monolayer of a certain width and speed. This layer can be formed either by a chute arrangement or by a belt arrangement. Each laser beam may be directed to the particles, when falling from the chute or belt, by a polygon mirror arrangement exciting or illuminating the particles of the feed. The light which is directly reflected by the surface of the particle as well as the light scattered within the particle, thus lighting up the area around the direct reflection, may be received via the same polygon mirror and may be measured by photo-electric elements converting the amount of light into an electrical signal. Each one of said photo-electric elements may for example be a respective photo-diode. The ratio of the reflection intensity and the scattering intensity may be determined by measuring the reflected light separately from the scattered light.

The signal coming from said detector may be related to or coupled with the position of the beam across the material stream. For example, the rotational position of the rotating polygon mirror may be used to determine which part of the material stream is currently being illuminated. Thus, two consecutive signals from the same sensor may be spatially related to each other in a known manner.

The signal coming from said detector may electronically modified, for example by multiplying it by a factor which is dependent on the position of the light band, so that a signal is obtained which does not depend on the position of the light band.

To detect diamonds in a product with uniform sensitivity, the light stream falling on said detector from the light scattered by part of the product may be adjusted in such a manner that it is independent of the position of said part in said detection zone. To this end, an adjusting element may be placed between said detector and the place where the product moves through the detection zone, the adjusting element letting through only some of the light scattered by a part the product, in such a manner that the light stream of the scattered light falling on said detector is independent of the position of said part. Said adjusting element can advantageously comprise a diaphragm with at least one calibrated opening. The diagram may have means to adjust the size of said opening. Said diaphragm could advantageously be provided with small, movable plates at the edge of said opening, where said plates enable the size and/or shape of the opening to be adjusted, in such a manner that the light stream falling on said detector is independent of the position of said light band.

Preferably scanning systems are provided to scan multiple faces of a rock particle simultaneously. A double scanning system may be used which comprises two scanning systems opposite to one another.

Through use of the methods and apparatus of the present invention, it is possible to reduce diamond breakage as compared with prior art diamond detection methods by ensuring diamond bearing rock can be recovered early before it is crushed. The present invention avoids the use of density media separation, which is known to have shortfalls in diamond recovery.

Furthermore, DMS is a costly stage in a recovery process due to the requirements of agents to adjust water density.

The present invention further maximizes the recovery of Type I & IIa diamonds. Prior art X-ray sorting can miss high quality diamonds having a low number of exclusions. The invention provides improved diamond recovery in ore bodies that exhibit poor preferential liberation factors. It may also be desirable to recover diamonds still attached to Kimberlite increasing their value as geological specimens, and the present invention may be used in this regard.

Itemized List of Embodiments

Item 1. A method for identifying a diamond signature comprising:
 illuminating a material with a multi-wavelength beam of Infrared, IR, light, wherein at least one of the multiple wavelengths is in the short wave infrared, SWIR, region;
 capturing SWIR reflections from light reflected by the material and producing a SWIR signal;
 capturing the remaining reflections from the material and producing an IR combined reflection and scatter signal;
 filtering out light scattered by the material from the light reflected by the material and capturing only the reflections of the incident beam, to produce an IR reflection signal;
 classifying the material as comprising diamond based on the presence of a diamond signature in the combination of the SWIR signal, the IR reflection signal and the IR combined reflection and scatter signal.

Item 2. The method of item 1 further comprising filtering out light having the same polarization as the incident beam, so that only cross-polarized light is captured.

Item 3. The method of item 1 or item 2 further comprising normalizing the SWIR signal and the IR combined reflection and scatter signal by dividing each by the IR reflection signal.

Item 4. The method of any preceding items further comprising scanning the beam across the material.

Item 5. The method of any preceding items wherein the material comprises at least one rock particle.

Item 6. The method of any preceding items wherein the two-dimensional space represents multiple rock particles.

Item 7. The method of any preceding items further comprising forming a two-dimensional space using the normalized SWIR signal and the normalized IR combined reflection and scatter signal to represent the material.

Item 8. The method of any preceding items further comprising classifying pixels within the two-dimensional space as diamond or other material classes.

Item 9. The method of any preceding items in use in a sorting process, wherein objects comprising material classified as diamond may be ejected from a flow path of objects to be sorted.

Item 10. An apparatus for identifying a diamond signature comprising:
  means for illuminating a material with a multi-wavelength beam of Infrared, IR, light, wherein at least one of the multiple wavelengths is in the short wave infrared, SWIR, region;
  means for capturing SWIR reflections from the light reflected by the material and means for producing a SWIR signal;
  means for capturing the remaining reflections from the material and means for producing an IR combined reflection and scatter signal;
  means for filtering out light scattered by the material from the light reflected by the material and means for capturing only the reflections of the incident beam, to produce an IR reflection signal;
  means for classifying the material as comprising diamond based on the presence of a diamond signature in the combination of the SWIR signal, the IR reflection signal and the IR combined reflection and scatter signal.

Item 11. The apparatus of item 10 further comprising a first IR laser and a second SWIR laser and means for combining multiple beams of IR light into one common beam.

Item 12. The apparatus of item 10 or item 11 further comprising means for scanning the beam across the material.

BRIEF DESCRIPTION OF THE DRAWINGS

Embodiments of the invention will be described, by way of example only, with reference to the accompanying drawings in which:

FIGS. 7b-d, 8b-d, and 9b-d are grayscale representations of the rock as captured by three different detectors used in the method of the invention.

DETAILED DESCRIPTION OF THE DRAWINGS

Figure 1:
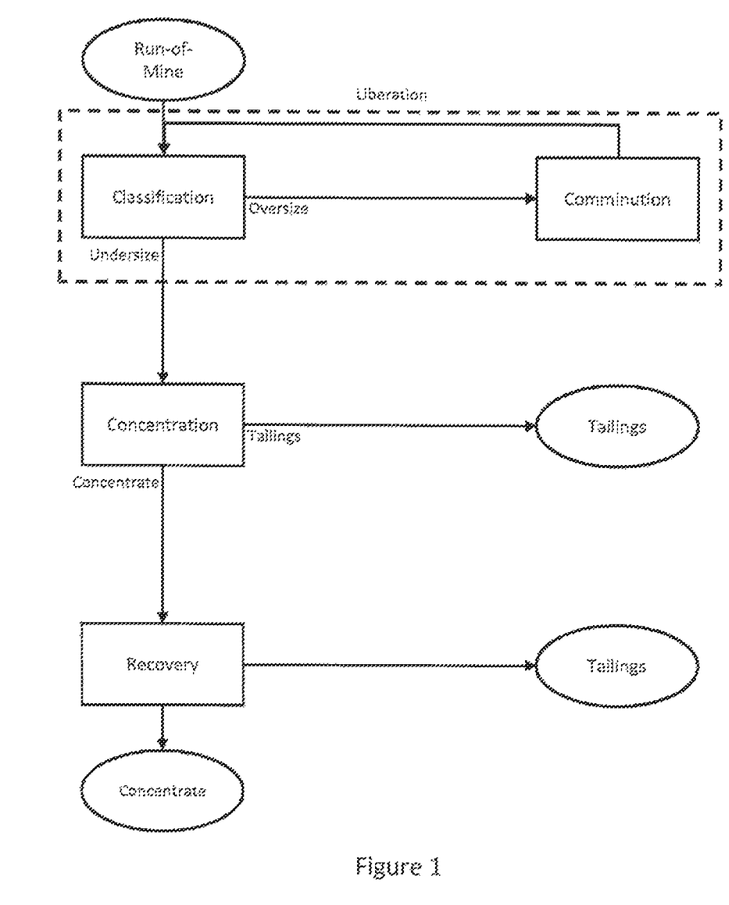
FIG. 1 is a flowchart representing a prior art diamond processing flow.

FIG. 1 is a flowchart representing a typical prior art diamond processing flow. The process is characterized by a liberation stage which incorporates size classification and comminution unit processes. The aim is to liberate the diamonds without damaging them. In a following concentration stage the classified material is reduced in mass to obtain a concentrate of smallest possible volume while retaining the highest possible percentage of diamonds. Finally, this concentrate is then treated in a recovery stage where a final concentrate is produced containing a marketable percentage of diamonds.

Figure 2:
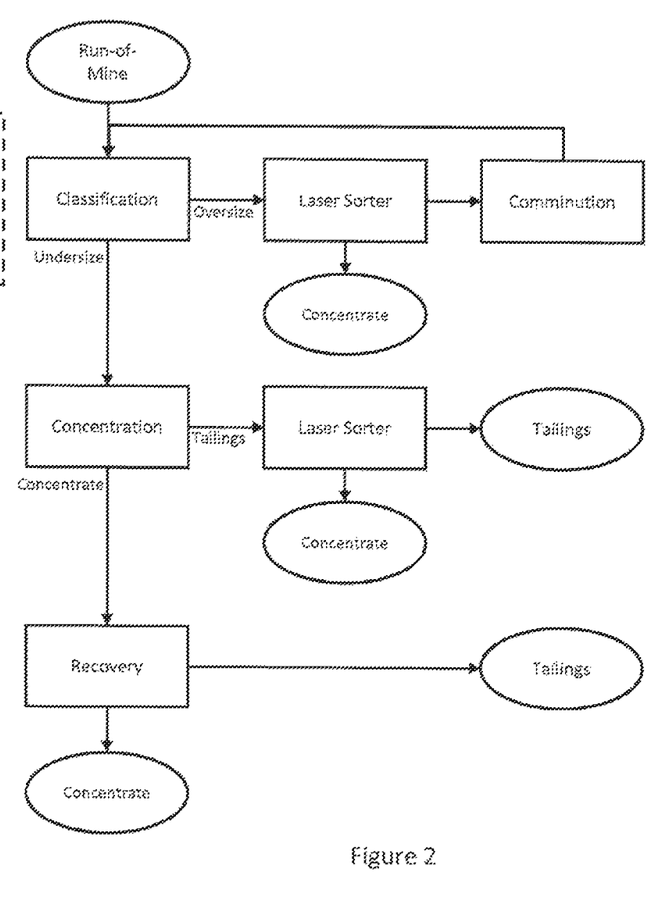
FIG. 2 is a flowchart representing an improved diamond processing flow into which the present invention may be incorporated.

The critical areas are diamond damage during liberation and loss of unliberated diamonds during concentration. These areas are addressed by the incorporation of a laser sorting unit in accordance with the present invention, as shown in FIG. 2. FIG. 2 is a flowchart representing an improved diamond processing flow into which the present invention may be incorporated. By incorporating a laser sorting process prior to comminution it is possible to recover liberated and unliberated diamonds in coarse size ranges before they are subjected to potentially damaging forces. The laser sorting can be applied up to 100 mm particle sizes, which makes it applicable even in primary crushing circuits.

The incorporation of a laser sorting process on the tailings of a concentration stage enables the recovery of lost liberated and unliberated diamonds. This can be achieved in size ranges down to 4 mm.

Figure 3:
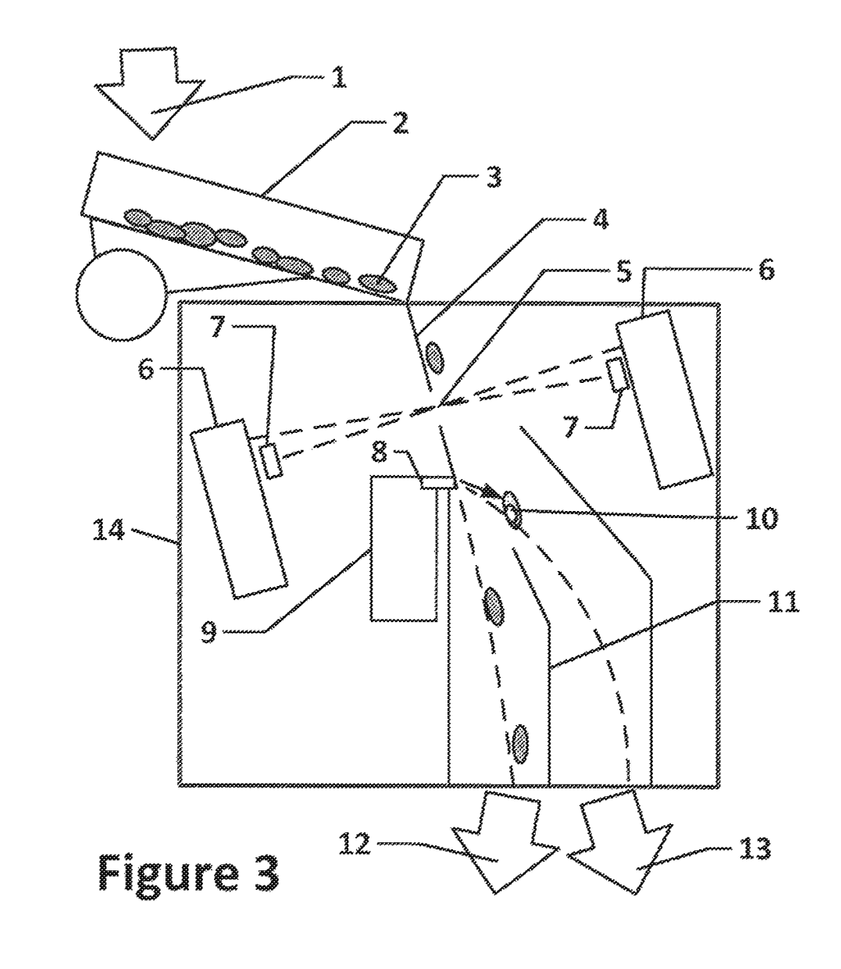
FIG. 3 illustrates one embodiment of a sorter system in accordance with the present invention.

FIG. 3 illustrates one embodiment of a sorter system in accordance with the present invention, suitable for use in a diamond processing flow.

The main frame 14 of the system represents the support structure for the material guidance, the laser scanner boxes and the ejection module. In the embodiment shown, a free fall arrangement with front and rear scanning capabilities is provided. The infeed 1 consisting of, for example, kimberlite rocks is fed on to a vibrating or shaking pan feeder 2. The purpose of this feeder is to distribute the infeed evenly to the full scanning and separation width of the equipment (typically 300 mm to 2000 mm wide) and further on to the acceleration chute 4. On this chute the material changes the feeding direction from a more horizontal orientation to a more vertical orientation guided by the chute 4 and is accelerated up to a speed on app. 3 m/s. By this acceleration process is spread even over the area available and most of the particles are liberated and do not touch each other. The scanning of the particles by mean of the laser scanners 7 from 2 opposite sides takes place in the gap in the chute forming the scanning zone 5. Another segment of the chute guides the particles further on the nozzle bar of the ejection module. In the case of the diamond recovery application one or more solenoid valves are activated releasing compressed air through the related nozzles 8 at the position where a potential liberated or non-liberated diamond 10 has been detected in order to push the particle over the splitter plate 11 which will be caught and guided to the eject outlet 13. All other Kimberlite particles will pass the nozzle bar without activation, will be dropped under the splitter plate and will finally be guided to the drop outlet 12 of the machine.

Figure 4:
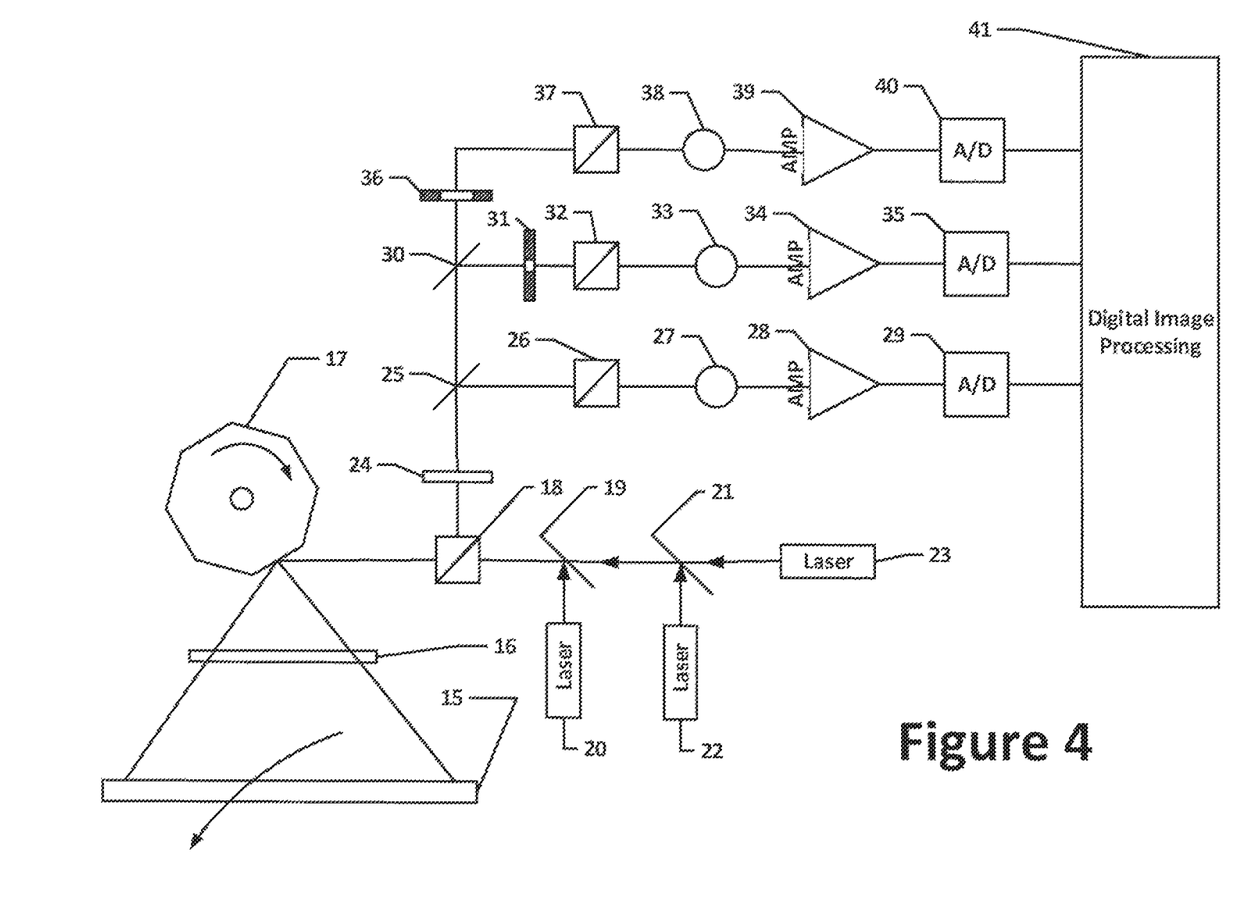
FIG. 4 shows one embodiment of an apparatus for identifying a diamond signature in accordance with the present invention.

FIG. 4 shows one embodiment of an apparatus for identifying a diamond signature in accordance with the present invention. This system may be incorporated in, or used in combination with, a sorter system, such as that shown in FIG. 3.

Three lasers 20, 22, 23 are provided in this embodiment, each producing a concentrated beam of light which is combined in one common beam by means of dichroic mirrors 19, 21. One laser provides an IR scatter-/anti-scatter laser beam. The second and the third lasers add wavelengths to support the discrimination of diamonds from all other translucent material, and where at least one of those emits a laser beam having a wavelength in the short wave infrared (SWIR) region. Each one of these laser beams is a monochromatic laser beam. More wavelengths can be added/mixed if appropriate to increase selectivity. The combined beam is guided to a polarizing beam splitter 18. The operating principles of a polarizing beam splitter are understood by those skilled in the art and a detailed explanation thereof is not necessary for purposes of this description. In general, although laser light is already polarized, and although the polarization of the combined light beam is oriented in such a way that it corresponds with the transmission polarization direction of the beam splitter, any irregularity or imperfection in the polarization of light beam is removed as light beam passes through the polarizing beam splitter 18. The combined light beam leaving polarizing beam splitter 18 is directed to a high speed rotating polygon mirror 17.

The high speed polygon mirror 17 directs the light beam (s) in a scanning plane over the full width of the scanning zone towards a reference or background element 15. It may be preferred to utilize a light gate 16 between the polygon mirror 17 and background element 15. This light gate 16 is described in detail in PCT application WO 98/44335. In general, the light gate 16 ensures that the light reflected back to the detectors from the scanned bodies is "independent" of the position of the bodies in the scanning pattern of the light beam(s). In this way, a substantially uniform sensitivity is obtained in scanning products across the full width of scanning plane. The light gate 16 may be made in the form of a diaphragm having an opening that narrows in the direction of the point of greatest reflected light from the scanned bodies (generally in the middle of the scanning plane). This opening is disposed in a plane perpendicular to the plane in which light beam moves. The form and size of the diaphragm opening are chosen so that whenever the light beam is directed towards the products, the signal generated by the detectors receiving the light "retuned" by the scanned products is independent of the position of the products within the scanning plane of the light beam.

Background element 15 may be made of various materials depending on the type of objects to be scanned, and is preferably of a color or structure which allows to discriminate all particles of the infeed from the background. The particles to be scanned pass through scanning zone between background element 15 and mirror 17.

In the scanning zone, the light beams impact on the products and a part of the light is reflected back to mirror 17 and polarizing beam splitter 18. The reflected light contains light having the same polarization as the incident light beam and light of perpendicular polarizations from the scanned bodies. The same polarized light is not particularly useful to the processing circuitry and may even mask certain useful information about the scanned products. Polarizing beam splitter 18 will split the reflected light into two polarization directions, one having the same polarization as the incident laser light, the polarization of which had been initially further aligned by the passage of the initial concentrated beam of light from lasers 20, 22, 23 through the same polarizing beam splitter 18, and the other having a 90-degree polarization (cross-polarized light) with respect to the incident laser light. The same polarized reflected light is passed directly through beam splitter 18 and is not further used. Thus, polarizing beam splitter 18 may be thought of as serving a "filtering" function in that it filters the same polarized light from the reflected light.

The cross polarized light from beam splitter 18 is directed to a focusing lens 24 and then to the dichroic mirror 25. For example, the SWIR wavelength can be reflected by this mirror and guided to the SWIR detector arrangement 27 which also includes the components 26, 28 and 29 whereas longer wavelengths pass through the dichroic mirror 25. The detector 27 produces a control signal proportional to the entire reflected cross polarized SWIR light field guided to an op-amp 28 and analogue/digital converter 29.

The light passing through the dichroic mirror 25 is guided to a non-polarizing beam splitter 30 (sometimes referred to in the art as a "50/50 beam splitter"). Beam splitter 30 passes about 50% of the cross polarized reflected light to the detector arrangement 33 which includes the components 31, 32, 34 and 35, and about 50% to the detector arrangement 38 which includes the components 37, 39 and 40. Each of the detector arrangements 33 and 38 have different field of views. Detector 38 has a field of view with a large enough diameter so that essentially all of the cross polarized light reflected from the scanned products, including the light diffused into translucent products (scattered light) and the relatively intense center light reflected from the point of impingement of the incident laser light on the product are captured. In another embodiment of the present invention, not shown herein, the detector 38 may be provided with a plate or diaphragm having a cross-sectional diameter the corresponds substantially to the cross-sectional diameter of the beam of cross-polarized light. Thus, it is possible to capture only the light which has been scattered by the product and optically filter out the light that has been directly reflected by the material.

As the intensity of the received light strongly depends on the brightness or reflectivity of the particle surface (dark surface gives a low signal, bright surface gives a high signal) an absolute measurement of the scattering effect is not possible. A reference channel is necessary allowing the relative measurement of the scattering effect. This reference channel is formed by the detector 38 arrangement measuring the combined reflected incident light and the scattered light. Detector 33 measures only the reflection of the incident light.

A simple equation allows for the normalization of the measuring using the two channels: Scattering normalized=direct reflection+scattering/direct reflection.

This normalized signal is independent of the surface brightness. The field of view of detector 38 is defined by an upstream defining member 36 such as a plate or diaphragm having a relatively large aperture or hole defined there through with a diameter that thus defines the diameter of the field of view. The detector 38 produces a control signal proportional to the entire reflected cross polarized light field guided to an op-amp 39 and analogue/digital converter 40. In one embodiment of the invention, the defining member 36 has a portion arranged to block out the relatively intense direct reflected light from the point of impact of the incident light beam on the products. In this embodiment, the reflected light is filtered from the scattered light and a scatter signal may be produced.

Detector 33 has a field of view corresponding in size essentially to the cross-sectional diameter of the incident scanning light beam. Detector 33 thus senses only the relatively intense direct reflected light from the point of impact of the incident light beam on the products. The field of view of detector 33 is defined by an upstream defining member 31 such as a plate or diaphragm having a hole or aperture defined there through with a diameter corresponding to the cross-sectional diameter of the incident laser light beam. The detector 33 produces an output signal proportional to the direct reflected light only guided to an op-amp 34 and analogue/digital converter 35.

All detectors have an upstream defining member 26, 32 and 37 which consists of a polarizing beam splitter in order guide only the cross polarized light to the detector. The digital signals of the three detector channels are acquired by the image processing system forming a two-dimensional image which represents the section of sorter feed traveling in between the scanning zone and the nozzle bar of the ejection module of the sorter. The image processing system evaluates the data in real time in order discriminate the particles from the background, to classify the particles and to control the valve block for those which should be ejected.

Figure 5:
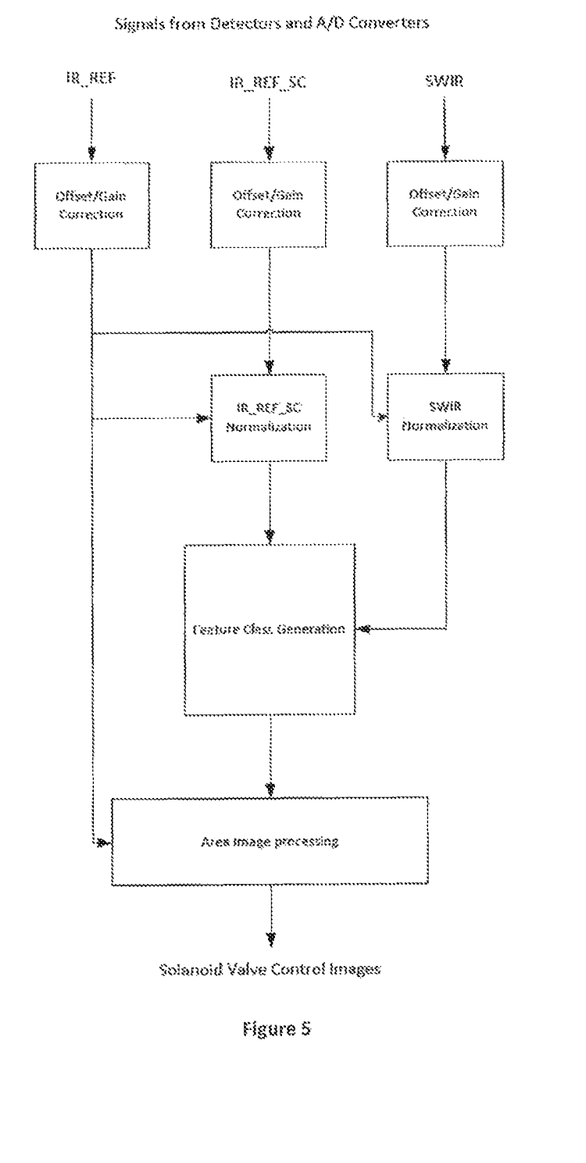
FIG. 5 is flow chart representing one embodiment of the processing of signals generated by the apparatus of FIG. 4 in accordance with a method of the present invention.

FIG. 5 is a flow chart of one embodiment of signal processing within an image processing system in accordance with the present invention.

FIG. 5 is flow chart representing one embodiment of the processing of signals generated by the apparatus of FIG. 4 in accordance with a method of the present invention, which may be carried out by an image processing system.

The following signal definitions apply to FIG. 5:

IR_REF: Infrared laser IR reflection signal (Detector 33)
IR_REF_SC: Infrared laser combined reflection and scatter signal (Detector 38)
SWIR: Short Wave Infrared laser signal (laser 22 plus laser 23 combined, Detector 27)

Normalization signals by brightness or respectively reflectivity:

IR_REF_SC'=IR_REF_SC/IR_REF
SWIR'=SWIR/IR_REF

In the process shown in FIG. 5, the three signals IR_REF, IR_REF_SC and SWIR of the appropriate detectors are converted by analogue/digital (ND) converters to digital values with a resolution of 12 bits. A control logic controls the conversion rate and timing as well as the synchronization with the rotating polygon mirror. As an example 2048 ND conversions take place per mirror face representing one scan over the full width of the material feed representing one line of 2048 pixels. The flow chart in FIG. 5 describes the functions performed on the pixel by pixel level before the area image processing takes place.

For each of the three signals an offset and gain correction is performed to make sure that the dark value is zero and the brightest value is 4095 (12-bit range). In order to get signals which are almost independent of the broad band reflectivity of the particle surface measured the digital values IR_REF_SC and SWIR are in the next stage normalized by dividing the values by the IR_REF signal.

Figure 6:
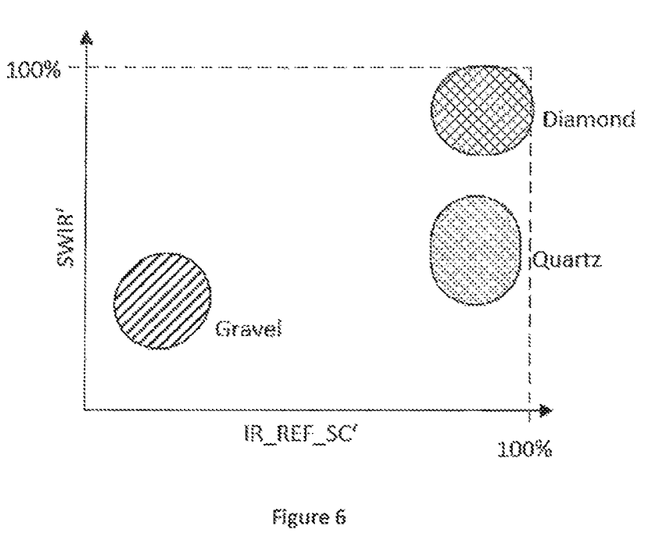
FIG. 6 is a definition used by a classification function to return a material class identifier whenever SWIR', IR_REF_SC' is member of Gravel, Quartz or Diamond, as used in the present invention.

For the feature class generation only the normalized values IR_REF_SC' and SWIR' are used to form a two-dimensional space, see FIG. 6. In this space the properties of the materials of interest to be discriminated can be describes as clouds of IR_REF_SC', SWIR' values per material forming a material definition space. Offline analyzing tools are uses to derive this definition space from representative samples and to setup the feature class generation function.

Once the feature class generation function is set up an actual pixel represented by the values IR_REF_SC' and SWIR' will form the input information. The classification function will return a material class identifier whenever SWIR', IR_REF_SC' is member of gravel, quartz or diamond according to the definition shown in FIG. 6. For example, the material class identifies may be 0 for gravel and 1 for quartz and 2 for diamond. More classes can be defined for other rock species in the material feed if appropriate.

For area image processing a two-dimensional picture in formed in the memory of the computing instance in order to be able to identify the particles and describe the distribution of feature classes on the particle surface. This need the discrimination of background vs. foreground pixels, which can for example be done by a simple threshold on the IR_REF signal. The final sorting decision on particle level, particle is "diamond" or respectively particle is "no diamond" is derived from the number of "gravel" pixels vs. the number of "diamond" pixels compared with a threshold. The Area Image Processing also generates the position and dimension information needed to control the solenoid valves of the rejectors individually and related to their position and size.

Figure 7A:
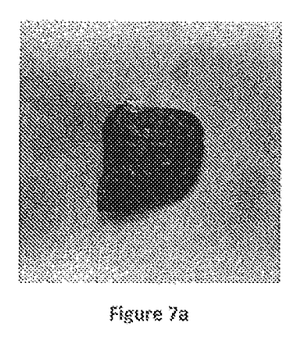
FIGS. 7a, 8a and 9a are photographs in normal ambient lighting, showing a respective rock particle comprising a partly liberated diamond.
Figure 8A:
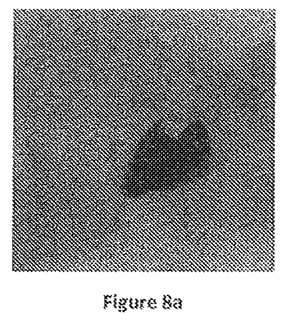
Figure 9A:
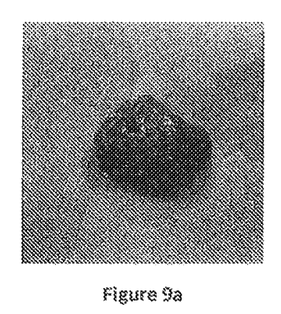

FIGS. 7a, 8a and 9a are photographs in normal ambient lighting, showing a respective rock particle comprising a partly liberated diamond. In FIG. 7a, the diamond is protruding from the rock in a way such that it is fairly easy to see with the naked eye. In FIG. 8a, the diamond is partially embedded inside the rock particle in a way such that it is more difficult to see than the diamond in FIG. 7a. In FIG. 9a, the diamond is almost completely embedded inside the rock particle and is therefore very difficult to see with the naked eye.

Figure 7B:
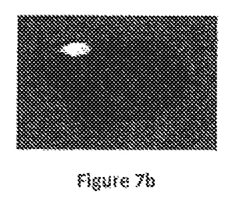
Figure 7C:
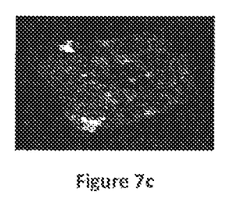
Figure 7D:
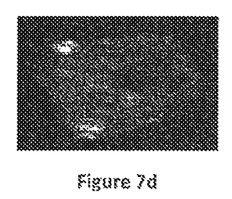
Figure 8B:
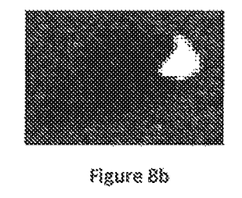
Figure 8C:
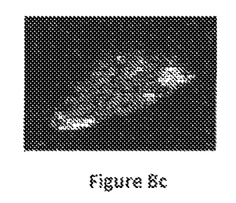
Figure 8D:
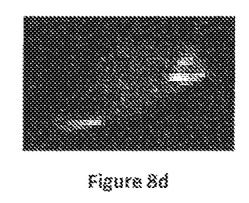
Figure 9B:
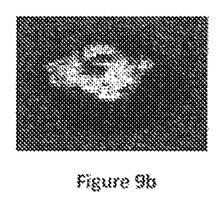
Figure 9C:
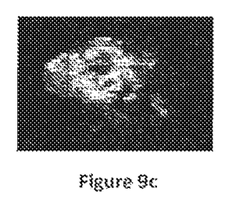
Figure 9D:
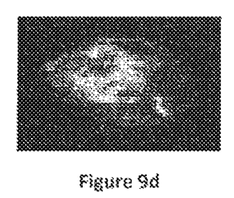

FIGS. 7b-d, 8b-d, and 9b-d are grayscale representations of the rock as seen by three different detectors used in the method of the invention. FIGS. 7b, 8b and 9b are grayscale representations of the rock according to the IR scatter signal, FIGS. 7c, 8c, and 9c are grayscale representations of the rock according to the IR reflection signal, and FIGS. 7d, 8d, and 9d are grayscale representations of the rock according to the SWIR signal.

Figure 7E:
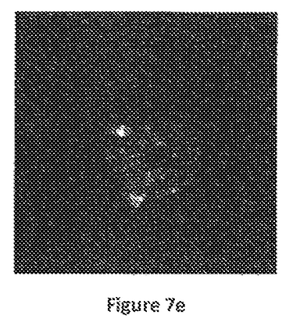
FIGS. 7e, 8e, and 9e show false-color representations of the respective rock based on the three grayscale representations of FIGS. 7b-d, 8b-d, and 9b-d.
Figure 8E:
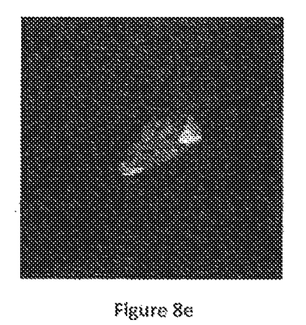
Figure 9E:
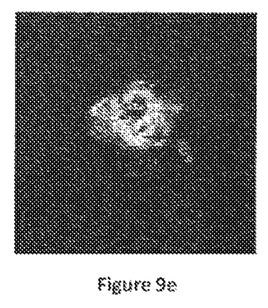

FIGS. 7e, 8e, and 9e show false-color representations of the respective rock using the three grayscale representations of FIGS. 7b-d, 8b-d, and 9b-d. In these figures, the IR scatter signal is mapped to the red channel, the IR reflection signal is mapped to the green channel, and the SWIR signal is mapped to the blue channel. Thus, a false-color RGB image is formed based on these three signals.

The representations of FIGS. 7*b-e*, 8*b-e*, and 9*b-e* are then used in the material classification of each pixel. This is e.g. done by applying threshold values to each one of the three grayscale representations, as well as to the false-color RGB image. If a pixel matches certain predetermined criteria, it is classified as comprising either rock, diamond, background material, another translucent material (e.g. quartz), or another material. This classification is done for all pixels in the four representations of the first rock particle.

Figure 7F:
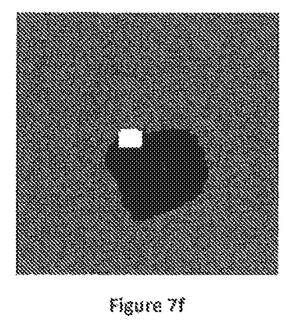
FIGS. 7f, 8f, and 9f are images showing the material classification of the rock particle of FIGS. 7a, 8a, and 9a, respectively.
Figure 8F:
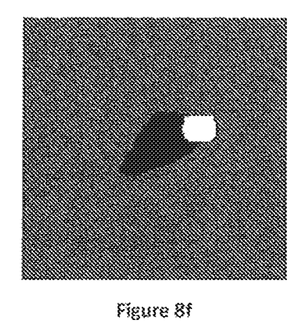
Figure 9F:
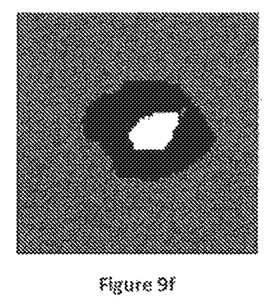

FIGS. 7*f*, 8*f*, and 9*f* are images showing the material classification of the first rock particle of FIGS. 7*a*, 8*a*, and 9*a*, respectively. The material classification is done by analyzing the IR scatter signal, the IR reflection signal, and the SWIR signal, e.g. as described above. In these figures, pixels classified as comprising the background material are colored gray, pixels classified as comprising the rock particle are colored black, and pixels classified as comprising diamond (due to the presence of a diamond signature in the signals analyzed) are colored white. The classification done in this step is used when determining which rock particles in a stream of rock particles should be ejected from the material stream. The classification is also used in directing the means for ejecting the rock particles classified as comprising diamond from the stream of material. As the ejection means are most suitably directed towards the center of the rock particle to which a diamond adheres, it is important to know the outlie of the rock particle as well as whether or not it comprises diamond.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A method for identifying the presence of partly liberated diamonds in a material stream, said method comprising the steps of:
    illuminating a material with a multi-wavelength beam comprising at least one monochromatic Short Wave Infrared (SWIR) laser beam, and at least one Infrared (IR) scatter-/anti-scatter laser beam,
    capturing a portion of said at least one monochromatic SWIR laser beam after said monochromatic SWIR laser beam has been reflected and/or scattered by the material,
    producing a SWIR signal based on the captured portion of said at least one monochromatic SWIR laser beam,
    capturing a first portion of said at least one IR scatter-/anti-scatter laser beam after said at least one IR scatter-/anti-scatter laser beam has been scattered and optionally reflected by the material,
    separating and thereafter capturing a reflected portion of said at least one IR scatter-/anti-scatter laser beam after said at least one IR scatter-/anti-scatter laser beam has been reflected by the material from a portion of said at least one IR scatter-/anti-scatter laser beam after said at least one IR scatter-/anti-scatter laser beam has been scattered by the material,
    producing an IR scatter signal based on said captured first portion of said at least one IR scatter-/anti-scatter laser beam,
    producing an IR reflection signal based on said captured reflected portion of said at least one IR scatter-/anti-scatter laser beam,
    classifying the material as comprising diamond based on the presence of a diamond signature in the combination of the SWIR signal, the IR reflection signal and the IR scatter signal.

2. The method of claim 1, further comprising the step of separating a first portion of said at least one IR scatter-/anti-scatter laser beam after said at least one IR scatter-/anti-scatter laser beam has been scattered by the material from a portion of said at least one IR scatter-/anti-scatter laser beam after said at least one IR scatter-/anti-scatter laser beam has been reflected by the material, and thereafter capturing said first portion of said at least one IR scatter-/anti-scatter laser beam.

3. The method of claim 1, wherein said at least one IR scatter-/anti-scatter laser beam is at least one monochromatic IR scatter-/anti-scatter laser beam.

4. The method of claim 1, further comprising the step of filtering out light having the same polarization as the incident beam, so that only cross-polarized light is captured.

5. The method of claim 1, wherein the step of separating a reflected portion of said IR scatter-/anti-scatter laser beam is done by optically filtering scattered light from reflected light.

6. The method of claim 1, further comprising the step of splitting said IR scatter-/anti-scatter laser beam.

7. The method of claim 1, further comprising the step of normalizing the SWIR signal and the IR scatter signal by dividing each by the IR reflection signal.

8. The method of claim 7, further comprising forming a two-dimensional space using the normalized SWIR signal and the normalized IR scatter signal to represent the material.

9. The method of claim 8, wherein the two-dimensional space represents multiple rock particles.

10. The method of claim 8, further comprising classifying pixels within the two-dimensional space as diamond or other material classes.

11. The method of claim 1, further comprising the step of scanning said multi-wavelength beam across said material stream.

12. The method of claim 1, wherein the material stream comprises at least one rock particle having a partly liberated diamond.

13. The method of claim 1, for use in a sorting process, further comprising ejecting objects comprising material classified as diamond from a transportation direction of said material stream.

14. A non-transitory computer readable medium containing program instructions which when executed by a processor cause the processor to perform the method of claim 1.

* * * * *